(12) United States Patent
Amano et al.

(10) Patent No.: US 6,515,188 B2
(45) Date of Patent: Feb. 4, 2003

(54) METHOD FOR PRODUCING 3-L-MENTHOXYPROPANE-1,2-DIOL

(75) Inventors: Akira Amano, Kanagawa (JP); Teruyoshi Akiyama, Kanagawa (JP); Takashi Miura, Kanagawa (JP); Toshimitsu Hagiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/115,096

(22) Filed: Apr. 4, 2002

(65) Prior Publication Data

US 2002/0156327 A1 Oct. 24, 2002

(30) Foreign Application Priority Data

Apr. 23, 2001 (JP) .................................. 2001-124134

(51) Int. Cl.$^7$ ................................... C07C 5/23
(52) U.S. Cl. ..................... 568/666; 560/231; 560/236; 568/670
(58) Field of Search ................ 560/231, 236; 568/666, 670

(56) References Cited

U.S. PATENT DOCUMENTS

| | | | |
|---|---|---|---|
| 4,459,425 A | 7/1984 | Amano, et al. | 568/666 |
| 5,245,048 A | 9/1993 | Rolfe et al. | 549/516 |
| 5,420,312 A | 5/1995 | Andrews et al. | 549/16 |
| 5,608,119 A | 3/1997 | Amano, et al. | 568/676 |
| 6,407,293 B1 * | 6/2002 | Amano | |

FOREIGN PATENT DOCUMENTS

| | | |
|---|---|---|
| EP | 1 201 635 A1 | 5/2002 |
| FR | 2 479 822 | 10/1981 |
| JP | 2-221 | 1/1990 |
| WO | WO00/43340 | 7/2000 |

* cited by examiner

*Primary Examiner*—Michael L. Shippen
(74) *Attorney, Agent, or Firm*—Fitzpatrick, Cella, Harper & Scinto

(57) ABSTRACT

A method for safely and efficiently producing high purity 3-l-menthoxypropane-1,2-diol and intermediates to be used in the method. As shown in the following reaction formula, 3-l-menthoxypropane-1,2-diol represented by the chemical formula (IV) is produced by adding l-menthol to a 1,2-epoxy-3-halogenopropane represented by the general formula (I) (wherein X represents a halogen atom) in an organic solvent in the presence of a Lewis acid, thereby producing a 1-halogeno-3-l-menthoxypropan-2-ol represented by the general formula (II), allowing the first intermediate to react with an alkali metal salt of an aliphatic carboxylic acid having from 1 to 5 carbon atoms to produce a 1-acyloxy-2-substituted-3-l-menthoxypropane represented by the general formula (III) and then hydrolyzing the second intermediate.

10 Claims, No Drawings

METHOD FOR PRODUCING 3-L-MENTHOXYPROPANE-1,2-DIOL

FIELD OF THE INVENTION

This invention relates to a method for producing 3-l-menthoxypropane-1,2-diol useful as, e.g., a cool-feeling agent or refreshment improving agent, and 1-acyloxy-2-substituted-3-l-menthoxypropanes useful as intermediates in producing the 3-t-menthoxypropane-1,2-diol and a production method thereof. According to the invention, 3-l-menthoxypropane-1,2-diol having high purity and 1-acyloxy-2-substituted-3-l-menthoxypropanes useful as synthetic intermediates of the 3-l-menthoxypropane-1,2-diol can be obtained by simple operation safely and with high yield.

In addition, according to the invention, (2S)-3-l-menthoxypropane-1,2-diol in which configuration of the 2-position of the propane moiety is controlled and which has more excellent refreshing feeling can be obtained with high optical purity.

BACKGROUND OF THE INVENTION 3-l-Menthoxypropane-1,2-diol is a known compound as is described in, e.g., JP-B-61-48813. 3-l-Menthoxypropane-1,2-diol is excellent in safety and has a property to provide l-menthol-like cool-feeling action on the skin and mucous membrane, while it is odorless and has no odor by itself unlike the case of l-menthol. Thus, when 3-l-menthoxypropane-1,2-diol is used, it does not exert influence on the aroma added to the product and can add cool-feeling action to the product. Accordingly, making use of these characteristics of 3-l-menthoxypropane-1,2-diol, it has been proposed to add 3-l-menthoxypropane-1,2-diol to oral compositions such as tooth powder and chewing gum and refreshments such as sherbet and hard candy, and also to aromatic cosmetics such as toilet articles (JP-A-60-25908, JP-A-63-208505), eye packs (JP-A-62-96403) and hair cosmetics (JP-A-62-192312), as well as aerosol compositions for anti-inflammatory drug and analgesic use (JP-A-63-264522).

Conventionally known methods for producing 3-l-menthoxypropane-1,2-diol include (i) a method in which l-menthol is made into sodium salt with metallic sodium or sodium hydride and then reacted with an allyl halide to produce 3-l-menthoxypropane-1-ene which is subsequently converted into an oxide by oxidizing it using an organic peroxide and then hydrolyzed (JP-B-61-48813); and (ii) a method in which l-menthol is added to benzyl glycidyl ether in the presence of a Lewis acid to produce 1-benzyloxy-3-l-menthoxypropan-2-ol which is then subjected to hydrogenolysis in the presence of a palladium-carbon catalyst to eliminate benzyl group (JP-A-7-82200).

However, in the conventional method (i), sodium salt of l-menthol is prepared using metallic sodium or sodium hydride, it has a problem of causing a danger of explosion and generation of hydrogen gas. What is more, since oxidation of 3-l-menthoxypropane-1-ene as the intermediate is carried out using an organic peroxide, it has a danger of causing explosion also from this point, so that this cannot be said as an industrially advantageous method, and there is room for further improvement from the economic point of view.

Also, since the conventional method (ii) is a production method aimed at synthesizing optically active substances, it is necessary to use expensive benzyl glycidyl ether. What is more, since the finally obtained 3-l-menthoxypropane-1,2-diol is contaminated with about 10% of 2-l-menthoxypropane-1,3-diol, it is necessary to carry out purification and fractionation by, e.g., a silica gel column chromatography so that it is difficult to obtain a large amount of 3-l-menthoxypropane-1,2-diol having high purity.

Also, in addition to these conventional methods, (iii) it has been proposed a method in which 1,2-epoxy-3-l-menthoxypropane as a synthetic intermediate of 3-l-menthoxypropane-1,2-diol is synthesized by allowing l-menthol to undergo addition reaction with a 1,2-epoxy-3-halogenopropane such as epichlorohydrin in an aqueous solution in the presence of a base and a quaternary ammonium salt [French Patent 2,479,822 (1981)]. However, it is known that a 1,2-epoxy-3-halogenopropane such as epichlorohydrin is unstable and apt to be decomposed in the presence of an acid or base ["Dictionary of Chemistry" p. 292, published by Tokyo Kagaku Dojin (1989)]. Thus, in the case of this method in which a 1,2-epoxy-3-halogenopropane is allowed to undergo the reaction in the presence of a base, the 1,2-epoxy-3-halogenopropane is decomposed when the reaction is carried out for a prolonged period of time, so that it is difficult to synthesize 1,2-epoxy-3-l-menthoxypropane in a large amount and this cannot be said as an industrially and economically advantageous method.

In addition, (iv) a method in which 1-allyloxy-3-chloro-2-propanol as an optically active glycerol derivative is produced by allowing epichlorohydrin and allyl alcohol to undergo the reaction in the presence of an acidic catalyst has been proposed as the reaction of epichlorohydrin with an alcohol (JP-A-2-221). However, this conventional method (iv) uses only primary allyl alcohol as the alcohol to be used in the reaction, and it does not report on the application to secondary alcohols, much less on the addition reaction with menthol.

Also, as another conventional method, it has been proposed (v) a method in which epichlorohydrin and alcohols are allowed to undergo the reaction in the presence of an acid catalyst and then subjected to an alkali treatment to effect ring closure, thereby converting into a glycidyl ether which is subsequently hydrolyzed, and then a glycerol ether is produced by heating the reaction mixture at a temperature of from 100 to 230° C. in the presence of a salt formed from a strongly basic compound and a weakly acidic compound (JP-A-2000-212114). However, in the case of this method, it is necessary to heat the reaction mixture at a high temperature of from 100 to 230° C., particularly from 150 to 200° C., in the presence of a salt formed from a strongly basic compound and a weakly acidic compound, in order to decompose the organic halogen contained in the hydrolysate of the glycidyl ether, so that this is not an efficient method. What is more, the alcohols used in this method are primary alcohols represented by a general formula: R-(OA)p-OH (wherein R represents a saturated or unsaturated, straight- or branched-chain hydrocarbon radical having from 1 to 36 carbon atoms, A represents an alkylene group having from 2 to 4 carbon atoms, and p is a number of from 0 to 100), and there is no disclosure on the use of secondary alcohols, much less on the use of menthol.

SUMMARY OF THE INVENTION

An object of the invention is to provide a method by which 3-l-menthoxypropane-1,2-diol having high purity can be produced by a simple process, safely and with a high yield.

Another object of the invention is to provide a synthetic intermediate useful in obtaining high purity 3-l-menthoxypropane-1,2-diol.

Still another object of the invention is to provide an efficient method for producing an intermediate useful in obtaining 3-l-menthoxypropane-1,2-diol.

A further object of the invention is to provide a method by which (2S)-3-l-menthoxypropane-1,2-diol whose configuration of the 2-position of the propane moiety is controlled and which has more excellent refreshing feeling can be produced with a high optical purity.

In order to achieve these objects, the present inventors have conducted extensive studies. As a result, they succeeded in producing a 1-acyloxy-2-substituted-3-l-menthoxypropanes as novel compounds, by producing a 1-halogeno-3-l-menthoxypropan-2-ol through the addition reaction of l-menthol with a 1,2-epoxy-3-halogenopropane in an organic solvent in the presence of a Lewis acid, and allowing the thus obtained 1-halogeno-3-l-menthoxypropan-2-ol to react with an aliphatic carboxylic acid alkali metal salt. After further studies, it was found that these novel 1-acyloxy-2-substituted-3-l-menthoxypropanes are chemically stable and can be preserved by themselves, and that the 3-l-menthoxypropane-1,2-diol of interest can be obtained conveniently with a high yield and a high purity by hydrolyzing these 1-acyloxy-2-substituted-3-l-menthoxypropanes.

Thereafter, the inventors have found that (2S)-3-l-menthoxypropane-1,2-diol whose configuration of the 2-position of the propane moiety is controlled and which has more excellent refreshing feeling can be produced with a high optical purity, by the use of an optically active substance as the 1-halogeno-3-l-menthoxypropan-2-ol, and have accomplished the invention based on these findings.

Accordingly, the invention is, (1) a method for producing 3-l-menthoxypropane-1,2-diol, which comprises adding l-menthol to a 1,2-epoxy-3-halogenopropane represented by the following general formula (I):

(I)

(wherein X represents a halogen atom)
in an organic solvent in the presence of a Lewis acid, thereby producing a 1-halogeno-3-l-menthoxypropan-2-ol represented by the following general formula (II):

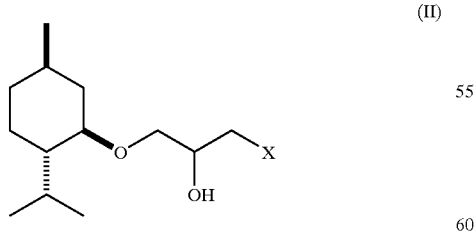

(II)

(wherein X represents a halogen atom),
subsequently reacting it with an alkali metal salt of an aliphatic carboxylic acid having from 1 to 5 carbon atoms, thereby producing a 1-acyloxy-2-substituted-3-l-menthoxypropane represented by the following general formula (III):

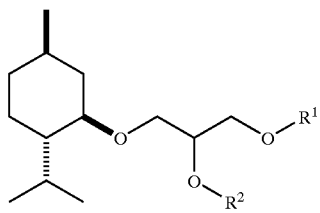

(III)

(wherein $R^1$ represents an acyl group derived from the aliphatic carboxylic acid having from 1 to 5 carbon atoms, and $R^2$ represents hydrogen atom or an acyl group derived from the aliphatic carboxylic acid having from 1 to 5 carbon atoms), and then hydrolyzing it to produce 3-l-menthoxypropane-1,2-diol represented by the following chemical formula (IV).

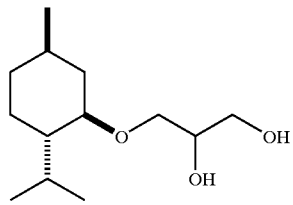

(IV)

Also, the invention is, (2) a method for producing 3-l-menthoxypropane-1,2-diol, which comprises reacting a 1-halogeno-3-l-menthoxypropan-2-ol represented by the following general formula (II):

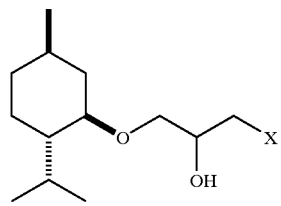

(II)

(wherein X represents a halogen atom) with an alkali metal salt of an aliphatic carboxylic acid having from 1 to 5 carbon atoms, thereby producing a 1-acyloxy-2-substituted-3-l-menthoxypropane represented by the following general formula (III):

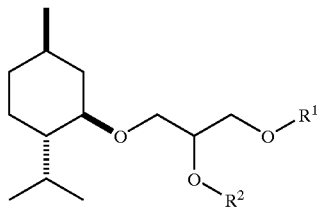

(III)

(wherein $R^1$ represents an acyl group derived from the aliphatic carboxylic acid having from 1 to 5 carbon atoms, and $R^2$ represents hydrogen atom or an acyl group derived from the aliphatic carboxylic acid having from 1 to 5 carbon atoms), and subsequently hydrolyzing it to produce 3-l-menthoxypropane-1,2-diol represented by the following chemical formula (IV):

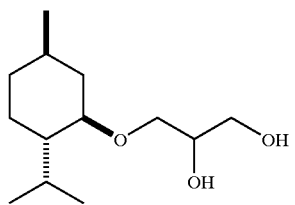

(IV)

Also, the invention is, (3) a method for producing a 1-acyloxy-2-substituted-3-l-menthoxypropane, which comprises reacting a 1-halogeno-3-l-menthoxypropan-2-ol represented by the following general formula (II):

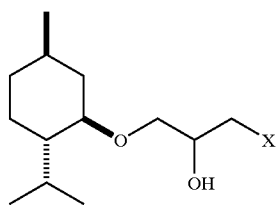

(II)

(wherein X represents a halogen atom) with an alkali metal salt of an aliphatic carboxylic acid having from 1 to 5 carbon atoms, thereby producing a 1-acyloxy-2-substituted-3-l-menthoxypropane represented by the following general formula (III):

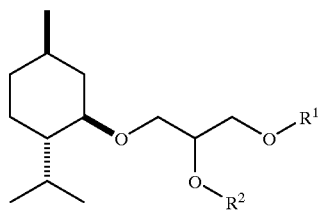

(III)

(wherein $R^1$ represents an acyl group derived from the aliphatic carboxylic acid having from 1 to 5 carbon atoms, and $R^2$ represents hydrogen atom or an acyl group derived from the aliphatic carboxylic acid having from 1 to 5 carbon atoms).

Also, the invention includes as preferred embodiments, (4) the production method according to any one of the above items (1) to (3), wherein X is chlorine atom in the 1,2-epoxy-3-halogenopropane represented by the general formula (I) and 1-halogeno-3-l-menthoxypropan-2-ol represented by the general formula (II);

(5) the production method according to any one of the above items (1) to (4), wherein configuration of the 2-position of the propane moiety is (R)-form in the 1,2-epoxy-3-halogenopropane represented by the general formula (I), and configuration of the 2-position of the propane moiety is (S)-form in the 1-halogeno-3-l-menthoxypropan-2-ol represented by the general formula (II), 1-acyloxy-2-substituted-3-l-menthoxypropane represented by the general formula (III) and 3-l-menthoxypropane-1,2-diol represented by the general formula (IV); and (6) the production method according to any one of the above items (1) to (5), wherein $R^1$ is acetyl group and $R^2$ is hydrogen atom or acetyl group in the general formula (III).

Also, the invention is, (7) a 1-acyloxy-2-substituted-3-l-menthoxypropane represented by the following general formula (III):

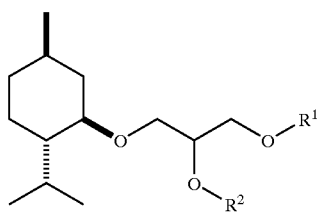

(III)

(wherein $R^1$ represents an acyl group derived from an aliphatic carboxylic acid having from 1 to 5 carbon atoms, and $R^2$ represents hydrogen atom or an acyl group derived from an aliphatic carboxylic acid having from 1 to 5 carbon atoms).

Also, the invention includes as preferred embodiments, (8) a 1-acetoxy-2-substituted-3-l-menthoxypropane represented by the following general formula (IIIa):

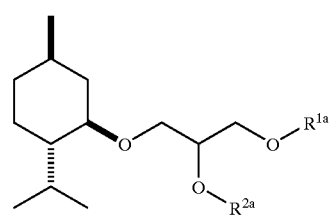

(IIIa)

(wherein $R^{1a}$ represents acetyl group, and $R^{2a}$ represents hydrogen atom or acetyl group);

(9) a (2S)-1-acyloxy-2-substituted-3-l-menthoxypropane represented by the following general formula (III'):

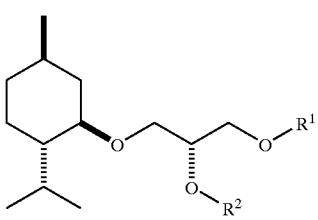

(III')

(wherein $R^1$ represents an acyl group derived from an aliphatic carboxylic acid having from 1 to 5 carbon atoms, and $R^2$ represents hydrogen atom or an acyl group derived from an aliphatic carboxylic acid having from 1 to 5 carbon atoms); and

(10) a (2S)-1-acetoxy-2-substituted-3-l-menthoxypropane represented by the following general formula (IIIa'):

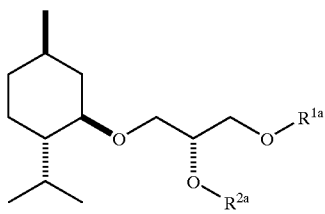

(wherein $R^{1a}$ represents acetyl group, and $R^{2a}$ represents hydrogen atom or acetyl group).

DETAILED DESCRIPTION OF THE INVENTION

The following describes the invention in detail.

The method of the invention for the production of 3-l-menthoxypropane-1,2-diol is carried out in accordance with the reactions shown below.

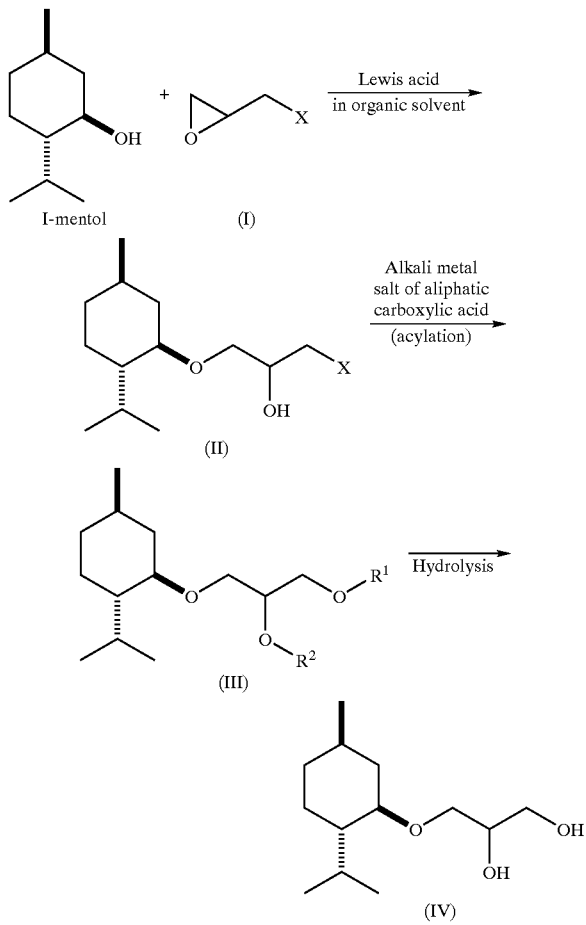

(In the formulae, X is a halogen atom, $R^1$ is an acyl group derived from an aliphatic carboxylic acid having from 1 to 5 carbon atoms, and $R^2$ is hydrogen atom or an acyl group derived from an aliphatic carboxylic acid having from 1 to 5 carbon atoms.)

That is, a novel 1-halogeno-3-l-menthoxypropan-2-ol (II) is produced by adding l-menthol to a 1,2-epoxy-3-halogenopropane (I) in an organic solvent in the presence of a Lewis acid. Next, the 1-halogeno-3-l-menthoxypropan-2-ol (II) is allowed to react with an alkali metal salt of an aliphatic carboxylic acid having from 1 to 5 carbon atoms to produce a 1-acyloxy-2-substituted-3-l-menthoxypropane (III) which is then hydrolyzed to obtain the 3-l-menthoxypropane-1,2-diol (IV).

Examples of the halogen atom X in the 1,2-epoxy-3-halogenopropane (I) include fluorine atom, chlorine atom, bromine atom and iodine atom. Illustrative examples of the 1,2-epoxy-3-halogenopropane include 1,2-epoxy-3-fluoropropane (epifluorohydrin), 1,2-epoxy-3-chloropropane (epichlorohydrin), 1,2-epoxy-3-bromopropane (epibromohydrin) and 1,2-epoxy-3-iodopropane (epiiodohydrin). Among them, 1,2-epoxy-3-chloropropane (epichlorohydrin) or 1,2-epoxy-3-bromopropane (epibromohydrin) in which the halogen atom X is chlorine atom or bromine atom is suitably used in the invention, and 1,2-epoxy-3-chloropropane (epichlorohydrin) is used more suitably.

Regarding the 1,2-epoxy-3-halogenopropane (I) and l-menthol as the material compounds, commercial products can be used as such.

In carrying out the reaction to add l-menthol to the 1,2-epoxy-3-halogenopropane (I), a method in which a Lewis acid is added to and dissolved in a solution prepared by dissolving l-menthol in an organic solvent, and then a solution prepared by dissolving the 1,2-epoxy-3-halogenopropane (I) in an organic solvent is added dropwise thereto to effect the reaction.

Regarding using ratio of the 1,2-epoxy-3-halogenopropane (I) and l-menthol, l-menthol is preferably from about 0.8 to 2 mol, more preferably from about 0.9 to 1.3 mol, based on 1 mol of the 1,2-epoxy-3-halogenopropane (I).

Also, amount of the Lewis acid to be used may be similar to the catalytically effective amount in the usual addition reaction and, generally, is preferably from about 0.01 to 0.1 mol, based on 1 mol of the 1,2-epoxy-3-halogenopropane (I).

Illustrative examples of the Lewis acid include boron trifluoride ether complex, aluminum chloride, zinc chloride, zinc bromide and ferric chloride, which may be used alone or as a mixture of two or more. Among them, aluminum chloride and/or boron trifluoride ether complex is preferably used from the viewpoint of easy handling and economically low price.

As the organic solvent, an organic solvent which does not exert influence of the addition reaction of l-menthol with the 1,2-epoxy-3-halogenopropane (I) is used, and its illustrative examples include aliphatic hydrocarbon solvents such as hexane, heptane and octane; alicyclic hydrocarbon solvents such as cyclohexane and methylcyclohexane; aromatic hydrocarbon solvents such as benzene, toluene and xylene; and petroleum ether solvents, which may be used alone or as a mixture of two or more. Among them, heptane and/or toluene is preferably used from the viewpoint of easy handling and economically low price.

Amount of the organic acid to be used is, in general, preferably from about 0.5 to 5 parts by volume, more preferably from about 1 to 3 parts by volume, based on 1 part by volume of l-menthol.

It is desirable to carry out the addition reaction of l-menthol to the 1,2-epoxy-3-halogenopropane (I) in an atmosphere of an inert gas such as nitrogen gas or argon gas for effecting smooth progress of the addition reaction.

Also, in carrying out the addition reaction by adding an organic solvent solution of the 1,2-epoxy-3-halogenopropane (I) dropwise to an organic solvent solution of l-menthol and a Lewis acid, the period of time for the dropwise addition of the 1,2-epoxy-3-halogenopropane (I)-dissolved organic solvent solution is generally preferably from about 0.5 to 10 hours, more preferably from about 1.5 to 3 hours.

A temperature of preferably from about 60 to 130° C., more preferably from about 65 to 120° C., is employed as the addition reaction temperature, and the 1-halogeno-3-l-menthoxypropan-2-ol (II) can be smoothly produced by carrying out the reaction at the temperature for about from 0.5 to 15 hours, preferably from about 1 to 5 hours, after completion of the dropwise addition of the organic solvent solution of 1,2-epoxy-3-halogenopropane (I).

The 1-halogeno-3-l-menthoxypropan-2-ol (II) obtained by this addition reaction is stable, generally shows an oily form and can be preserved.

Accordingly, the 1-halogeno-3-l-menthoxypropan-2-ol (II) obtained by the addition reaction may be preserved after purifying it by, e.g., distillation or a column chromatography, or without carrying out the purification treatment, and then used by collecting it from a preservation container at the time of the production of the 1-acyloxy-2-substituted-3-l-menthoxypropane (III) or 3-l-menthoxypropane-1,2-diol (IV). Alternatively, the 1-halogeno-3-l-menthoxypropan-2-ol (II) formed by the addition reaction may be cooled as occasion demands and then directly used in the subsequent reaction without carrying out after-treatment such as purification.

In the above reaction, configuration of the 2-position of the propane structure can be controlled without racemization by the use of an optically active 1,2-epoxy-3-halogenopropane (I). Illustratively, by the use of a (2R)-1,2-epoxy-3-halogenopropane (I'), it can be easily introduced into a (2S)-1-halogeno-3-l-menthoxypropan-2-ol (II'). Also, when a (2S)-1,2-epoxy-3-halogenopropane (I') is used, it can be easily introduced into a (2R)-1-halogeno-3-l-menthoxypropan-2-ol (II').

By allowing the 1-halogeno-3-l-menthoxypropan-2-ol (II) obtained by the addition reaction to react with an alkali metal salt of an aliphatic carboxylic acid having from 1 to 5 carbon atoms, the 1-acyloxy-2-substituted-3-l-menthoxypropane (III) is produced.

As the alkali metal salt of an aliphatic carboxylic acid having from 1 to 5 carbon atoms to be used in this reaction, a lithium, sodium or potassium salt of an aliphatic carboxylic acid having from 1 to 5 carbon atoms is suitably used. The illustrative examples thereof include lithium formate, lithium acetate, lithium propionate, lithium butyrate, lithium isobutyrate, lithium valerate, lithium isovalerate, lithium pivalate, sodium formate, sodium acetate, sodium propionate, sodium butyrate, sodium isobutyrate, sodium valerate, sodium isovalerate, sodium pivalate, potassium formate, potassium acetate, potassium propionate, potassium butyrate, potassium isobutyrate, potassium valerate, potassium isovalerate and potassium pivalate, which may be used alone or as a mixture of two or more. Among them, one or two or more of sodium formate, potassium formate, sodium acetate and potassium acetate are preferably used, and sodium acetate is used more preferably, from the viewpoint of easy handling and economically low price.

When an alkali metal salt of an aliphatic carboxylic acid having 6 or more carbon atoms or an aromatic carboxylic acid alkali metal salt is used, solid precipitation becomes considerable so that the 1-acyloxy-2-substituted-3-l-menthoxypropane (III) cannot be produced smoothly.

From the economical point of view, amount of the used alkali metal salt of an aliphatic carboxylic acid having from 1 to 5 carbon atoms is from about 1.0 to 5.0 mol, particularly from about 1.05 to 2.0 mol, based on 1 mol of the 1-halogeno-3-l-menthoxypropan-2-ol (II).

It is desirable that the used alkali metal salt of an aliphatic carboxylic acid having from 1 to 5 carbon atoms is in an anhydrous state, because the 1-acyloxy-2-substituted-3-l-menthoxypropane (III) can be formed with a high yield and the yield becomes stable.

According to the invention, a commercially available alkali metal salt of an aliphatic carboxylic acid having from 1 to 5 carbon atoms can be used as such or by subjecting it to a dehydration treatment in advance.

According to the invention, the reaction of the 1-halogeno-3-l-menthoxypropan-2-ol (II) with an alkali metal salt of an aliphatic carboxylic acid having from 1 to 5 carbon atoms, for producing the 1-acyloxy-2-substituted-3-l-menthoxypropane (III), can be carried out under joint use of an aliphatic carboxylic acid anhydride as occasion demands.

As the aliphatic carboxylic acid anhydride, an aliphatic carboxylic acid anhydride having from 2 to 5 carbon atoms is suitably used, and its illustrative examples include acetic anhydride, propionic anhydride, butyric anhydride, isobutyric anhydride, valeric anhydride, isovaleric anhydride and pivalic anhydride, which may be used alone or as a mixture of two or more. Among them, acetic anhydride is preferably used.

When an aliphatic carboxylic acid anhydride is jointly used, its amount to be used is preferably from 1.0 to 5.0 mol, more preferably from about 1.05 to 2.0 mol, based on 1 mol of the 1-halogeno-3-l-menthoxypropan-2-ol (II).

According to the invention, a commercially available aliphatic carboxylic acid anhydride can be used as such.

In addition, according to the invention, the reaction of the 1-halogeno-3-l-menthoxypropan-2-ol (II) with an alkali metal salt of an aliphatic carboxylic acid having from 1 to 5 carbon atoms, for producing the 1-acyloxy-2-substituted-3-l-menthoxypropane (III), may also be carried out in the presence of a phase transfer catalyst as occasion demands.

When the reaction is carried out in the presence of a phase transfer catalyst, a reaction rate improving effect is obtained.

As the phase transfer catalyst, a quaternary ammonium salt is suitably used, and its illustrative examples include quaternary ammonium salts which can be industrially easily obtained, such as tetramethylammonium chloride, tetrabutylammonium bromide, tetraethylammonium iodide, tetrabutylammonium iodide, trimethylhexadecylammonium chloride, dimethyldioctylammonium chloride, trimethylbenzylammonium chloride and trioctylmethylammonium chloride, which may be used alone or as a mixture of two or more. Among them, tetramethylammonium bromide is preferably used from the viewpoint of easy handling and economically low price.

When production reaction of the 1-acyloxy-2-substituted-3-l-menthoxypropane (III) is carried out in the presence of a phase transfer catalyst, the amount of the phase transfer catalyst to be used is preferably from about 0.01 to 0.2 mol, more preferably from about 0.02 to 0.05 mol, based on 1 mol of the 1-halogeno-3-l-menthoxypropan-2-ol (II).

A commercially available phase transfer catalyst can be used as such.

Production reaction of the 1-acyloxy-2-substituted-3-l-menthoxypropane (III) may be carried out in the absence of solvent or using a solvent.

When a solvent is used, any solvent which does not significantly inhibit the production reaction of 1-acyloxy-2-substituted-3-l-menthoxypropane (III) can be used, but an organic solvent is suitably used. Illustrative examples of the suitably used organic solvent include aliphatic hydrocarbon solvents such as hexane, heptane and octane; alicyclic hydrocarbon solvents such as cyclohexane and methylcyclohexane; aromatic hydrocarbon solvents such as benzene, toluene and xylene; ether solvents such as diethyl ether, diisopropyl ether, dimethoxyethane, tetrahydrofuran, dioxane and 1,3-dioxofuran; amide solvents such as dimethylformamide, dimethylacetamide and N-methylpyrrolidone; and petroleum ether solvents, which may be used alone or as a mixture of two or more. Among them, dimethylformamide is preferably used from the viewpoint of smooth progress of the reaction, good handling and economically low price.

Amount of the organic acid to be used is preferably from about 1 to 10 parts by volume, more preferably from about 2 to 5 parts by volume, based on 1 part by volume of the 1-halogeno-3-l-menthoxypropan-2-ol (II).

It is desirable to carry out the production reaction of 1-acyloxy-2-substituted-3-l-menthoxypropane (III) in an atmosphere of an inert gas such as nitrogen or argon.

It is desirable to carry out the reaction for the production of the 1-acyloxy-2-substituted-3-l-menthoxypropane (III) at a temperature of from about 60 to 200° C., particularly from about 80 to 170° C., and the 1-acyloxy-2-substituted-3-l-menthoxypropane (III) can be smoothly produced by carrying out the reaction for a period of from about 0.5 to 20 hours, preferably from about 1 to 10 hors, while keeping this temperature.

The reaction temperature and reaction time can be optionally changed and adjusted depending on the kind and amount of the used alkali metal salt of an aliphatic carboxylic acid having from 1 to 5 carbon atoms.

The 1-acyloxy-2-substituted-3-l-menthoxypropane (III) obtained by this reaction is a single product of 1-acyloxy-3-l-menthoxypropan-2-ol (III-A) in which only the 1-position of the propane moiety is substituted by an acyloxy group, a single product of 1,2-diacyloxy-3-l-menthoxypropane (III-B) in which the 1-position and 2-position of the propane moiety are substituted by an acyloxy group, or a mixture of the (III-A) and (III-B). Forming ratio of the (III-A) and (III-B) in 1-acyloxy-2-substituted-3-l-menthoxypropane (III) changes depending on the kind and amount of the alkali metal salt of an aliphatic carboxylic acid having from 1 to 5 carbon atoms and the presence or absence, kind and amount of the other components which are used as occasion demands (e.g., an aliphatic carboxylic acid anhydride and a phase transfer catalyst). When the reaction is carried out using only an alkali metal salt of an aliphatic carboxylic acid having from 1 to 5 carbon atoms without using an aliphatic carboxylic acid anhydride and a phase transfer catalyst, ration of the 1-acyloxy-3-l-menthoxypropan-2-ol (III-A) generally becomes 80% or more. On the other hand, when an aliphatic carboxylic acid anhydride is jointly used, ratio of the 1,2-diacyloxy-3-l-menthoxypropane (III-B) increases as the amount of the aliphatic carboxylic acid anhydride increases.

The 1-acyloxy-2-substituted-3-l-menthoxypropane (III) obtained by the reaction is a novel compound which is generally in an oily form and can be preserved.

The thus obtained 1-acyloxy-2-substituted-3-l-menthoxypropane (III) may be preserved after purifying it by, e.g., distillation or a column chromatography treatment, or without carrying out the purification treatment, and then used by collecting it from a preservation container at the time of the production of the 3-l-menthoxypropane-1,2-diol (IV). Alternatively, the 1-acyloxy-2-substituted-3-l-menthoxypropane formed by the reaction may be cooled as occasion demands and then directly used in the production of the 3-l-menthoxypropane-1,2-diol (IV) without carrying out after-treatment such as purification.

In the reaction, when an optically active 1-halogeno-3-l-menthoxypropan-2-ol (II) is used and allowed to react with an alkali metal salt of an aliphatic carboxylic acid having from 1 to 5 carbon atoms in the absence of an aliphatic carboxylic acid anhydride, an optically active 1-acyloxy-3-l-menthoxypropan-2-ol (III-A) in which configuration of the 2-position of the propane moiety is controlled highly selectively can be obtained without racemization. Illustratively, when a (2S)-1-halogeno-3-l-menthoxypropan-2-ol (II') is used and allowed to react with an alkali metal salt of an aliphatic carboxylic acid having from 1 to 5 carbon atoms in the absence of an aliphatic carboxylic acid anhydride, it can be introduced into a (2S)-1-acyloxy-2-substituted-3-l-menthoxypropane (III-A'). Also, when a (2R)-1-halogeno-3-l-menthoxypropan-2-ol (II") is used and allowed to react with an alkali metal salt of an aliphatic carboxylic acid having from 1 to 5 carbon atoms in the absence of an aliphatic carboxylic acid anhydride, it can be introduced into a (2R)-1-acyloxy-2-substituted-3-l-menthoxypropane (III-A").

Illustrative examples of the 1-acyloxy-2-substituted-3-l-menthoxypropane (III) formed by the reaction include the 2-position racemic bodies and optically active substances [(2S)-form and (2R)-form] of the propane structure of 1-acyloxy-3-l-menthoxypropan-2-ols such as 1-formyloxy-3-l-menthoxypropan-2-ol, 1-acetoxy-3-l-menthoxypropan-2-ol, 1-butyryloxy-3-l-menthoxypropan-2-ol, 1-isobutyryloxy-3-l-menthoxypropan-2-ol, 1-valeryloxy-3-l-menthoxypropan-2-ol, 1-isovaleryloxy-3-l-menthoxypropan-2-ol and 1-pivaloyloxy-3-l-menthoxypropan-2-ol; and 1,2-diacyloxy-3-l-menthoxypropanes such as 1,2-diformyloxy-3-l-menthoxypropane, 1,2-diacetoxy-3-l-menthoxypropane, 1,2-dipropionyloxy-3-l-menthoxypropane, 1,2-dibutyryloxy-3-l-menthoxypropane, 1,2-diisobutyryloxy-3-l-menthoxypropane, 1,2-divaleryloxy-3-l-menthoxypropane, 1,2-diisobutyryloxy-3-l-menthoxypropane, 1,2-diisovaleryloxy-3-l-menthoxypropane and 1,2-dipivaloyloxy-3-l-menthoxypropane.

By hydrolyzing the 1-acyloxy-2-substituted-3-l-menthoxypropane (III) obtained by the reaction, 3-l-menthoxypropane-1,2-diol (IV) is formed.

It is desirable to carry out hydrolysis of the 1-acyloxy-2-substituted-3-l-menthoxypropane (III) in the presence of a base. As the base to be used in the hydrolysis, hydroxides, carbonates and/or alkoxides of an alkali metal or alkaline earth metal are suitably used. Their illustrative examples include lithium hydroxide, sodium hydroxide, potassium hydroxide, calcium hydroxide, barium hydroxide, lithium carbonate, sodium carbonate and potassium carbonate, which may be used alone or as a mixture of two or more. Among them, sodium hydroxide and/or potassium hydroxide is preferably used from the viewpoint of smooth progress of the hydrolysis and economically low price.

It is desirable to add the base to the reaction system in the form of aqueous solution. It is desirable that concentration of the base aqueous solution is a high concentration of 40% by mass or more, particularly from 45 to 55% by mass, because the hydrolysis reaction smoothly progresses thereby.

Amount of the base to be used is preferably from about 1.0 to 5.0 mol, particularly from about 1.5 to 3.0 mol, based on 1 mol of the 1-acyloxy-2-substituted-3-l-menthoxypropane (III).

It is desirable to carry out the hydrolysis reaction of 1-acyloxy-2-substituted-3-l-menthoxypropane (III) in an organic solvent. Examples of the organic solvent include alcohol solvents such as methanol, ethanol, propanol, isopropanol and butanol; and ether solvents such as diisopropyl ether, dimethoxyethane, tetrahydrofuran, dioxane and 1,3-dioxofuran, which may be used alone or as a mixture of two or more. Among them, methanol and/or ethanol is preferably used from the viewpoint of economically low price.

Amount of the organic acid to be used is preferably from about 1 to 10 parts by volume, more preferably from about 2 to 5 parts by volume, based on 1 part by volume of the 1-acyloxy-2-substituted-3-l-menthoxypropane (III).

Temperature of the hydrolysis reaction of 1-acyloxy-2-substituted-3-l-menthoxypropane (III) is preferably from about 20 to 100° C., particularly from about 50 to 80° C., and the 3-l-menthoxypropane-1,2-diol (IV) is formed by carrying out the reaction for a period of from about 0.5 to 5 hours, preferably from about 1 to 3 hours, while keeping this temperature. Recovery of 3-l-menthoxypropane-1,2-diol (IV) from the reaction products containing 3-l-menthoxypropane-1,2-diol (IV) can be carried out by a usual method. Though not particularly limited, e.g., when a hydrophilic organic solvent is used in the reaction, 3-l-menthoxypropane-1,2-diol (IV) can be recovered as a concentrated product by, after adding water to the reaction products as occasion demands, evaporating the hydrophilic organic solvent used in the reaction, adding an acid aqueous solution and a hydrocarbon organic solvent such as hexane, butane, benzene, toluene or xylene to the reaction mixture, carrying out extraction of 3-l-menthoxypropane-1,2-diol (IV) with an organic solvent while carrying out neutralization of the used base as occasion demands, and then evaporating the solvent. Purification of 3-l-menthoxypropane-1,2-diol (IV) can be carried out, e.g., by distillation or a column chromatography treatment.

In the hydrolysis reaction, when an optically active 1-acyloxy-3-l-menthoxypropan-2-ol (III-A) is used, it can be introduced into a 3-l-menthoxypropane-1,2-diol (IV) in which configuration of the 2-position of the propane moiety is controlled can be obtained without carrying out racemization. Illustratively, when a (2S)-1-acyloxy-3-l-menthoxypropan-2-ol (III-A') is used, it can be easily introduced into a (2S)-3-l-menthoxypropane-1,2-diol (IV'). Also, when a (2R)-1-acyloxy-3-l-menthoxypropan-2-ol (III-A") is used, it can be easily introduced into a (2R)-3-l-menthoxypropane-1,2-diol (IV").

Among members of the 3-l-menthoxypropane-1,2-diol (IV), a (2S)-3-l-menthoxypropane-1,2-diol (IV') in which configuration of the 2-position of the propane structure is controlled has more excellent refreshing feeling. According to the invention, when (2R)-1,2-epoxy-3-halogenopropane is used as the 1,2-epoxy-3-halogenopropane (I) and allowed to react with l-menthol in the presence of a Lewis acid, it can be introduced easily into a (2S)-1-halogeno-3-l-menthoxypropan-2-ol (III'), the (2S)-1-halogeno-3-l-menthoxypropan-2-ol (II') can be then easily introduced into a (2S)-1-acyloxy-2-substituted-3-l-menthoxypropane (III') by allowing it to react with an alkali metal salt of an aliphatic carboxylic acid having from 1 to 5 carbon atoms, and then the (2S)-3-l-menthoxypropane-1,2-diol (IV) having excellent refreshing feeling can be easily obtained by hydrolyzing the (2S)-1-acyloxy-2-substituted-3-l-menthoxypropane (III').

Making use of the characteristics of the thus obtained 3-l-menthoxypropane-1,2-diol (IV), such as cool-feeling action, refrigerant action, odorless property and safety, it is used in various applications such as toiletry products, bathing articles, food and drink and medicaments, and their examples include various lotions such as whole body lotion, after-shave lotion and hair lotion; skin cosmetics such as washing cream, vanishing cream, cleansing cream, cold cream, milky lotion, beauty wash, pack, make remover and lip cream; poultices, adhesive preparations, nasal hyperemia removers and antiperspirants; hair care articles such as shampoo, rinse, treatment and conditioner; hair cosmetics such as hair tonic, hair cream and hair spray; perfumes and eau de Colognes; bathing articles, body shampoo and soap; shaving foams and gels; detergents and softeners; interior aromatics; dentifrice; mouth cleaners; ointments; and food and drink such as soft drinks, chewing gums, candies, ice creams, sherbets, jelly, tablets and troches.

The following describes the invention illustratively with reference to Examples, but the invention is not restricted by the following Examples.

In this connection, the apparatus used for the measurement (analysis) of physical properties in the following examples is as follows.

(1) Chemical Purity:

Gas chromatography "HP6890" column mfd. by HEWLETT PACKARD

Column; "NEUTRABOND-1" mfd. by GL Science (inner diameter×length=0.25 mm×30 m)

(2) Nuclear Magnetic Resonance Spectrum:

$^1$H-NMR; "DRX-500" mfd. by Brucker (500 MHz)

(3) Infrared Absorption Spectrum (IR):

Equipment: "Nicolet AVATAR 360" mfd. by Nicolet Japan

Measuring method: NaCl film method (4) Mass Spectrum (MS):

M-80 mass spectrometer: mfd. by Hitachi (ionization voltage 20 eV)

(5) Polarimeter;

"DIP-360" mfd. by Japan Spectroscopic

EXAMPLE 1

Synthesis of 1-Chloro-3-l-menthoxypropan-2-ol (1) In an atmosphere of nitrogen, 136.7 g (0.8763 mol) of l-menthol (mfd. by Takasago International Corporation) and 295 ml of n-heptane were put into a reaction flask (500 ml capacity) and dissolved at room temperature. Next, 3.5 g (26.88 mmol) of anhydrous aluminum chloride was added thereto and dissolved under stirring, and the solution was heated to 70° C. A 61 g (0.6572 mol) portion of epichlorohydrin was added dropwise to this solution at the same temperature maintaining 2 hours. After completion of the dropwise addition, the reaction was carried out at the same temperature for 7 hours. Thereafter, the reaction mixture was cooled to room temperature.

(2) The reaction mixture obtained in (1) was washed with water and then with 10% sodium carbonate aqueous solution, and n-heptane was evaporated to obtain an oily substance. By distilling this oily substance under a reduced pressure, 57.2 g (0.37 mol) of un-reacted l-menthol was recovered at a boiling point of from 78 to 99° C./600 Pa (4.5 mmHg), and then 117 g of 1-chloro-3-l-menthoxypropan-2-ol (chemical purity 97.86%) was obtained as a colorless and transparent oil (yield 70% based on epichlorohydrin) at a boiling point of from 98° C./35 Pa (0.26 mmHg) to 121° C./25 Pa (0.19 mmHg).

(3) Analytical results of the 1-chloro-3-l-menthoxypropan-2-ol obtained in (2) were as follows.

$[\alpha]_D^{25}$: −73.7° (c=1.05, EtOH); MS (m/e): 248 (M$^+$), 165, 163, 139, 138, 123, 109, 97, 95, 83, 81, 71, 69, 57, 55, 53, 43, 41, 29, 27; IR (neat, cm$^{-1}$): 3422, 2955, 2922, 2869, 1456, 1385, 1370, 1344, 1180, 1114, 1067, 1050, 1011, 991, 974, 922, 845, 753; $^1$H-NMR (CDCl$_3$; δ ppm): 0.78 (3 H, d, J=6.9), 0.81–0.88 (2H, m), 0.90 (3H, d, J=7.0), 0.93 (3H, d, J=6.5), 0.96–1.01 (1H, m), 1.20–1.26 (1H, m), 1.30–1.40 (1H, broad), 1.61–1.66 (2H, m), 2.09 (1H, m), 2.14 (1H, m), 2.52 (1H, d, J=5.9), 3.09 (1H, dt, J=10.6, 4.1), 3.44 (1H, dd, J=9.4, 5.2), 3.60 (1H, dd, J=11.0, 5.6), 3.73 (1H, dd, J=9.4, 5.2), 3.91–3.97 (1H, m).

EXAMPLE 2

Synthesis of 1-Acetoxy-3-l-menthoxypropan-2-ol

In an atmosphere of nitrogen, 20 g of the 1-chloro-3-l-menthoxypropan-2-ol obtained in Example 1 (chemical purity 97.86%, 78.78 mmol), 7.13 g (86.92 mmol) of anhydrous sodium acetate and 0.51 g (1.582 mmol) of tetrabutylammonium bromide were put into a reaction flask (100 ml capacity) and then allowed to undergo the reaction at 150 to 160° C. for 4 hours. Thereafter, the reaction mixture was cooled to 50° C. or less.

(2) The reaction mixture obtained in (1) was mixed with 30 ml of water and 50 ml of heptane to effect separation, the organic layer was washed with saturated brine and dried with anhydrous sodium sulfate, and then the solvent was recovered to obtain an oily substance. By distilling this oily substance under a reduced pressure, partially purified 1-acetoxy-3-l-menthoxypropan-2-ol was obtained at a boiling point of from 111 to 120° C./25 Pa (0.19 mmHg). Composition of this product when analyzed by the gas chromatography was composed of 5.53% by mass of 3-l-menthoxypropane-1,2-diol, 86.04% by mass of 1-acetoxy-3-l-menthoxypropan-2-ol (yield 92.38% based on 1-chloro-3-l-menthoxypropan-2-ol) and 5.13% by mass of 1,2-diacetoxy-3-l-menthoxypropane.

(3) A 15 g portion of the partially purified product obtained in (2) was purified by a silica gel column chromatography. As the developing solvent, a mixed solvent composed of ethyl acetate and hexane was used, and the mixing ratio of ethyl acetate was gradually increased from 4% by volume to 10% by volume. By this, 1-acetoxy-3-l-menthoxypropan-2-ol was eluted with the most high purity in a fraction obtained by a developing solvent containing from 6 to 10% by volume of ethyl acetate. After separating and recovering the solvent from this fraction, the residue was distilled under a reduced pressure to obtain 7.74 g (chemical purity 99.72%) of 1-acetoxy-3-l-menthoxypropan-2-ol as a colorless and transparent oil at a boiling point of from 123 to 124° C./32 Pa (0.24 mmHg).

(4) Analytical results of the 1-acetoxy-3-l-menthoxypropan-2-ol obtained in (3) were as follows.

$[\alpha]_D^{25}$: −67.8° (c=1.0, EtOH); MS (m/e): 169, 155, 139, 138, 123, 117, 97, 95, 83, 81, 69, 57, 55, 43, 41; IR (neat, cm$^{-1}$): 3461, 2955, 2869, 1743, 1456, 1371, 1344, 1181, 1110, 1044, 973, 921, 846; $^1$H-NMR (CDCl$_3$; δ ppm): 0.78 (3H, d, J=6.9), 0.80–0.88 (2H, m), 0.88–0.90 (3 H, d, J=6.9), 0.91–0.92 (3H, d, J=6.7), 0.93–1.00 (1H, m), 1.19–1.27 (1H, m), 1.30–1.39 (1H, broad), 1.59–1.68 (2H, m), 2.04–2.10 (1H, m), 2.09 (3H, s), 2.11–2.18 (1H, m), 2.59 (0.5H, s), 2.60 (0.5H, s), 3.04–3.11 (1H, m), 3.33 (0.25H, dd, J=9.5, 7.8), 3.37 (0.25H, dd, J=9.4, 7.05), 3.62 (0.25H, dd, J=9.3, 7.65), 3.70 (0.25H, dd, J=9.4, 6.85), 3.97 (1H, m), 4.10–4.19 (2H, m).

EXAMPLE 3

Synthesis of 1-Formyloxy-3-f-menthoxypropan-2-ol

1-Formyloxy-3-l-menthoxypropan-2-ol was obtained with a yield of 60.9% by carrying out the reaction under the same conditions as in Example 2, except that anhydrous sodium formate was used instead of anhydrous sodium acetate.

EXAMPLE 4

Synthesis of 1,2-Diacetoxy-3-l-menthoxypropane (1) In a stream of nitrogen, 100 g of 1-chloro-3-l-menthoxypropan-2-ol obtained by the method of Example 1 (chemical purity 97.86%, 393.6 mmol), 36 g (438.9 mmol) of anhydrous sodium acetate and 56.3 g (550 mmol) of acetic anhydride were put into a reaction flask (200 ml capacity) and then allowed to undergo the reaction at 135 to 145° C. for 7 hours. Thereafter, the reaction mixture was cooled to room temperature.

(2) The reaction mixture obtained in (1) was poured into 528 g (498 mmol) of 10% sodium carbonate aqueous solution to neutralize acetic acid and acetic anhydride. After separation of layers by adding 200 ml of toluene, the organic layer was washed with saturated brine and dried with anhydrous sodium sulfate, and then the solvent was recovered to obtain an oily substance. By distilling this oily substance under a reduced pressure, 113.5 g (chemical purity 98.3%) of 1,2-diacetoxy-3-l-menthoxypropane was obtained as a colorless and transparent oil at a boiling point of 119° C./26 Pa (0.20 mmHg) (yield 93.4% based on 1-chloro-3-l-menthoxypropan-2-ol).

(3) Analytical results of the 1,2-diacetoxy-3-l-menthoxypropane obtained in (2) were as follows.

$[\alpha]_D^{25}$: −60.5° (c=1.0, EtOH); MS (m/e): 271, 254, 194, 181, 159, 139, 138, 117, 95, 83, 81, 69, 57, 55, 43, 41; IR (neat, cm$^{-1}$): 2960, 2920, 2870, 1750, 1245, 1225, 1115, 1050, 963, 850; $^1$H-NMR (CDCl$_3$; δ ppm): 0.76 (3H, d, J=7.0), 0.80–0.88 (2H, m), 0.88 (3H, d, J=7.1), 0.91 (3H, d, J=6.5), 0.93–0.99 (1H, m), 1.18–1.25 (1H, m), 1.33 (1H, m), 1.60–1.66 (2H, m), 2.01–2.07 (1H, m), 2.05 (3H, s), 2.07 (3H, s), 2.13 (1H, m), 3.03 (1H, m), 3.40–3.46 (1H , m), 3.71–3.76 (1H, m), 4.15–4.21 (1H, m), 4.31–4.35 (1H, m), 5.09–5.18 (1H, m).

EXAMPLE 5

Synthesis of 3-l-Menthoxypropane-1,2-diol (1) In a stream of nitrogen, 100 g of 1-chloro-3-l-menthoxypropan-2-ol obtained by the method of Example 1 (chemical purity 97.86%, 395.1 mmol), 35.65 g (434.6 mmol) of anhydrous sodium acetate and 2.547 g (7.9 mmol) of tetrabutylammonium bromide were put into a reaction flask (300 ml capacity) and then allowed to undergo the reaction at 150 to 160° C. for 5 hours. Thereafter, the reaction mixture was cooled to 50° C. or less.

(2) In a stream of nitrogen, the reaction mixture cooled to 50° C. or less obtained in (1) was mixed with a mixed solution prepared in advance from 18.91 g (472.75 mmol) of sodium hydroxide, 85.1 ml of water and 85.1 ml of methanol, and the resulting mixture was heated under reflux for 1 hour. After completion of the reaction, this was again heated to evaporate methanol. Thereafter, this was cooled to 50° C. or less, mixed with 750 ml of water and 150 ml of toluene to effect separation of layers, the thus obtained organic layer was washed twice with 10% brine and dried with anhydrous magnesium sulfate, and then the solvent was recovered to obtain an oily substance. By distilling this oily substance under a reduced pressure, 88.17 g (chemical purity 97.09%) of 3-l-menthoxypropane-1,2-diol was obtained as a colorless and transparent oil at a boiling point of from 112 to 118° C./26 Pa (0.20 mmHg) (yield 94.2% based on 1-chloro-3-l-menthoxypropan-2-ol).

(3) Analytical results of the 3-l-menthoxypropane-1,2-diol obtained in (2) were as follows.

$[\alpha]_D^{25}$: −84.17° (c=1.03, EtOH); MS (m/e): 230 (M$^+$), 215, 169, 155, 139, 138, 123, 109, 97, 95, 83, 81, 71, 69, 57, 55, 43, 41; IR (neat, cm$^{-1}$): 3385, 2954, 2869, 1455, 1369, 1349, 1240, 1185, 1110, 1091, 1054, 920, 850; $^1$H-NMR (CDCl$_3$; δ ppm): 0.77 (3H, d, J=7.0), 0.80–0.88 (2H, m), 0.88–0.92 (3H, m), 0.92–0.99 (1H, m), 1.19–1.25 (1H, m), 1.35 (1H, m), 1.59–1.66 (2H, m), 2.06–2.11 (1H, m), 2.13 (1H, s), 2.34–2.60 (2H, broad), 3.03–3.10 (1H, m), 3.33–3.42 (1H, m), 3.61–3.72 (3H, m), 3.80–3.84 (1H, m).

EXAMPLE 6

Synthesis of 3-l-Menthoxypropane-1,2-diol

In a stream of nitrogen, 10 g of 1-acetoxy-3-l-menthoxypropan-2-ol obtained by the method of Example 2 (chemical purity 99.72%, 36.60 mmol), 1.76 g (43.9 mmol) of sodium hydroxide, 10 ml of water and 10 ml of methanol were put into a reaction flask (100 ml capacity) and then heated under reflux for 1 hour. Thereafter, this was treated by the same method of Example 3(2) to obtain 8.15 g (chemical purity 98.8%) of 3-l-menthoxypropane-1,2-diol as a colorless and transparent oil (yield 95.5% based on 1-acetoxy-3-l-menthoxypropan-2-ol).

EXAMPLE 7

Synthesis of 3-l-Menthoxypropane-1,2-diol

In a stream of nitrogen, 10 g of 1,2-diacetoxy-3-l-menthoxypropane obtained by the method of Example 4 (chemical purity 98.3%, 32.24 mmol), 3.10 g (77.38 mmol) of sodium hydroxide, 10 ml of water and 10 ml of methanol were put into a reaction flask (100 ml capacity) and then heated under reflux for 1 hour. Thereafter, this was treated by the same method of Example 3(2) to obtain 7.15 g (chemical purity 97.8%) of 3-l-menthoxypropane-1,2-diol as a colorless and transparent oil (yield 96.8% based on 1-acetoxy-3-l-menthoxypropan-2-ol).

EXAMPLE 8

Synthesis of (2S)-1-Chloro-3-l-menthoxypropan-2-ol (1) In a stream of nitrogen, 8.5 g (54.53 mmol) of l-menthol (mfd. by Takasago International Corporation), 6.5 ml of n-heptane and 219 mg (1.64 mmol) of anhydrous aluminum chloride were put into a reaction flask (30 ml capacity) and dissolved under stirring, and the solution was heated to 70° C. A 3.8 g (41 mmol) portion of (2R)-(−)-epichlorohydrin (mfd. by Daiso, optical purity 99% ee) was added dropwise to this solution at the same temperature maintaining 2 hours. After completion of the dropwise addition, the reaction was carried out at the same temperature for 5 hours. Thereafter, the reaction mixture was cooled to room temperature. This reaction mixture was washed with water and dried with anhydrous magnesium sulfate, and then the solvent was recovered to obtain an oily substance. This oily substance was distilled under a reduced pressure to recover l-menthol and then further distilled to obtain 6.8 g of (2S)-1-chloro-3-l-menthoxypropan-2-ol (chemical purity 97.74%) as a colorless and transparent oil (yield 65.07% based on epichlorohydrin) at a boiling point of 101° C./36 Pa (0.27 mmHg).

(2) Analytical results of the (2S)-1-chloro-3-l-menthoxypropan-2-ol obtained in (1) were as follows.

$[\alpha]_D^{25}$: −85.98° (c=1.02, EtOH); $^1$H-NMR (CDCl$_3$; δ ppm): 0.78 (3H, d, J=6.9), 0.81–0.88 (2H, m), 0.90 (3H, d, J=7.3), 0.92 (3H, d, J=6.6), 0.94–1.10 (1H, m), 1.21–1.27 (1H, m), 1.35 (1H, m, broad), 1.59–1.67 (2H, m), 2.06–2.10 (1H, m), 2.11–2.17 (1H, m), 2.54 (1H, d, J=5.8), 3.10 (1H, dt, J=10.6, 4.2), 3.42 (1H, dd, J=9.5, 5.1), 3.59 (1H, dd, J=11.0, 5.7), 3.65 (1H, dd, J=11.0, 5.8), 3.73 (1H, dd, J=9.5, 4.5), 3.93 (1H, m).

EXAMPLE 9

Synthesis of (2S)-3-l-Menthoxypropane-1,2-diol (1) In a stream of nitrogen, 5 g of (2S)-1-chloro-3-l-menthoxypropan-2-ol obtained by the method of Example 8 (chemical purity 97.47%, 19.60 mmol), 1.77 g (21.6 mmol) of anhydrous sodium acetate and 126 mg (0.4 mmol) of tetrabutylammonium bromide were put into a reaction flask (10 ml capacity) and then allowed to undergo the reaction at 160° C. for 4 hours. Thereafter, the reaction mixture was cooled to 50° C. or less.

(2) In a stream of nitrogen, the reaction mixture cooled to 50° C. or less obtained in (1) was mixed with 944 mg (23.6 mmol) of sodium hydroxide and 10 ml of 50% aqueous ethanol prepared in advance, and the resulting mixture was heated under reflux for 2.5 hours. After completion of the reaction, ethanol was evaporated under a reduced pressure. Thereafter, this was mixed with 150 ml of heptane to effect separation of layers, the thus obtained organic layer was washed with saturated brine and dried with anhydrous magnesium sulfate, and then the solvent was recovered to obtain an oily substance. By distilling this oily substance under a reduced pressure, 3.63 g (chemical purity 97.06%) of (2S)-3-l-menthoxypropane-1,2-diol was obtained as a colorless and transparent oil at a boiling point of 125° C./41 Pa (0.31 mmHg) (yield 78.06% based on (2S)-1-chloro-3-l-menthoxypropan-2-ol).

(3) Analytical results of the (2S)-3-l-menthoxypropane-1,2-diol obtained in (2) were as follows.

$[\alpha]_D^{25}$: −89.410 (c=1.02, EtOH); $^1$H-NMR (CDCl$_3$; δ ppm): 0.78 (3H, d, J=7.0), 0.81–0.88 (2H, m), 0.90 (3H, d, J=7.2), 0.92 (3H, d, J=6.6), 0.93–1.00 (1H, m), 1.21–1.27 (1H, m), 1.35 (1H, m, broad), 1.59–1.68 (2H, m), 2.07–2.11 (1H, m), 2.11–2.17 (1H, m), 2.49 (1H, s), 3.08 (1H, dt, J=7.0, 4.1), 3.37 (1H, dd, J=9.4, 6.1), 3.65 (1H, dd, J=11.5, 5.5), 3.72 (2H, dd), 3.83 (1H, m).

(4) A mixed solution of 210 mg (0.913 mmol) of (2S)-3-l-menthoxypropane-1,2-diol obtained in (2), 100 mg (1.19 mmol) of n-pentanal and 2 ml of hexane was mixed with 10 mg of p-toluenesulfonic acid monohydrate and heated under reflux for 1 hour. This was cooled to room temperature, neutralized with 5% sodium carbonate aqueous solution, washed with water and then subjected to a gas chromatography analysis by employing the following conditions to find that its optical purity was 99.30%.

GLC Analysis:

Column: Neutrabound-1, 0.25 mm×30 (mfd. by G L Science)

Column temperature: 180 to 240° C. (programming rate: 4° C./minute)

Detection temperature: 240° C.

According to the method of the invention, 3-l-menthoxypropane-1,2-diol useful, e.g., as a cool-feeling agent and a refrigerant improving agent, can be produced safely by a simple operation with high yield and high purity without using unstable and explosion-causing materials such as metallic sodium, sodium hydride and peroxides, so that this is an industrially advantageous method.

Also, according to the invention, (2S)-3-l-menthoxypropane-1,2-diol in which configuration of the 2-position of the propane structure is controlled and which has more excellent refreshing feeling can be obtained with high optical purity by the use of an optically active 1,2-epoxy-3-halogenopropane (I) as the material.

Also, according to the invention, a 1-halogeno-3-l-menthoxypropan-2-ol as an intermediate for the production of 3-l-menthoxypropane-1,2-diol can be produced safely by a simple operation with high yield and high purity without using undesirable materials such as metallic sodium, sodium hydride and peroxides, by adding l-menthol to a 1,2-epoxy-3-halogenopropane in an organic solvent in the presence of a Lewis acid.

Also, according to the invention, a 1-acyloxy-2-substituted-3-l-menthoxypropane as a novel intermediate for the production of 3-l-menthoxypropane-1,2-diol can be produced safely with high yield and high purity, by a simple operation in which a 1-halogeno-3-l-menthoxypropan-2-ol is allowed to react with an alkali metal salt of an aliphatic carboxylic acid having from 1 to 5 carbon atoms.

In addition, the novel 1-acyloxy-2-substituted-3-l-menthoxypropane of the invention is useful as an intermediate for the production of 3-l-menthoxypropane-1,2-diol.

While the invention has been described in detail and with reference to specific embodiments thereof, it will be apparent to one skilled in the art that various changes and modifications can be made therein without departing from the scope thereof.

This application is based on Japanese patent application No. 2001-124134 filed Apr. 23, 2001, the entire contents thereof being hereby incorporated by reference.

What is claimed is:

1. A method for producing 3-l-menthoxypropane-1,2-diol, which comprises adding l-menthol to a 1,2-epoxy-3-halogenopropane represented by the following general formula (I):

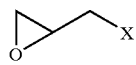

(I)

(wherein X represents a halogen atom) in an organic solvent in the presence of a Lewis acid, thereby producing a 1-halogeno-3-l-menthoxypropan-2-ol represented by the following general formula (II):

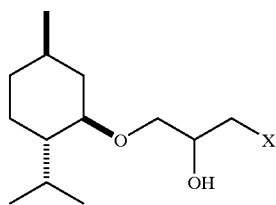

(II)

(wherein X represents a halogen atom),
subsequently reacting it with an alkali metal salt of an aliphatic carboxylic acid having from 1 to 5 carbon atoms, thereby producing a 1-acyloxy-2-substituted-3-l-menthoxypropane represented by the following general formula (III):

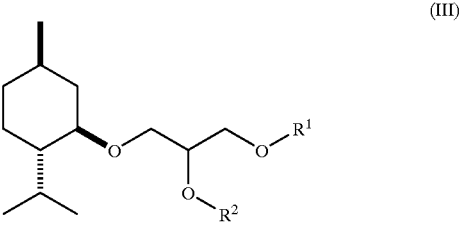

(III)

(wherein $R^1$ represents an acyl group derived from the aliphatic carboxylic acid having from 1 to 5 carbon atoms, and $R^2$ represents hydrogen atom or an acyl group derived from the aliphatic carboxylic acid having from 1 to 5 carbon atoms), and then hydrolyzing it to produce 3-l-menthoxypropane-1,2-diol represented by the following chemical formula (IV):

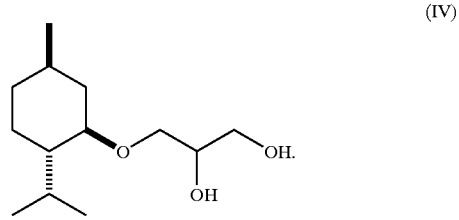

(IV)

2. A method for producing 3-l-menthoxypropane-1,2-diol, which comprises reacting a 1-halogeno-3-l-menthoxypropan-2-ol represented by the following general formula (II):

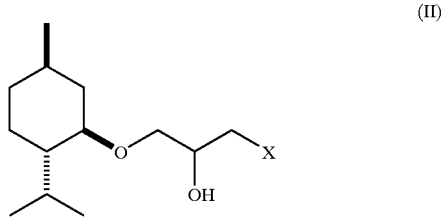

(II)

(wherein X represents a halogen atom) with an alkali metal salt of an aliphatic carboxylic acid having from 1 to 5 carbon atoms, thereby producing a 1-acyloxy-2-substituted-3-l-menthoxypropane represented by the following general formula (III):

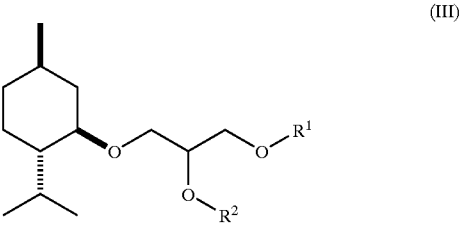

(III)

(wherein $R^1$ represents an acyl group derived from the aliphatic carboxylic acid having from 1 to 5 carbon atoms, and $R^2$ represents hydrogen atom or an acyl group derived from the aliphatic carboxylic acid having from 1 to 5 carbon atoms), and subsequently hydrolyzing it to produce 3-l-menthoxypropane-1,2-diol represented by the following chemical formula (IV):

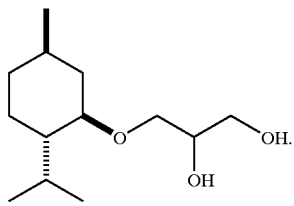
(IV)

3. A method for producing a 1-acyloxy-2-substituted-3-l-menthoxypropane, which comprises reacting a 1-halogeno-3-l-menthoxypropan-2-ol represented by the following general formula (II):

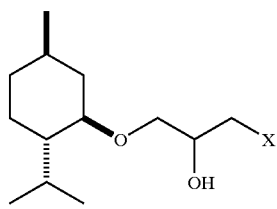
(II)

(wherein X represents a halogen atom) with an alkali metal salt of an aliphatic carboxylic acid having from 1 to 5 carbon atoms, thereby producing a 1-acyloxy-2-substituted-3-l-menthoxypropane represented by the following general formula (III):

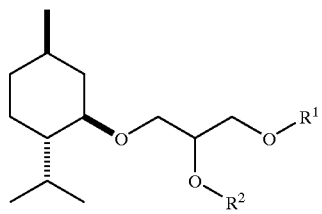
(III)

(wherein $R^1$ represents an acyl group derived from the aliphatic carboxylic acid having from 1 to 5 carbon atoms, and $R^2$ represents hydrogen atom or an acyl group derived from the aliphatic carboxylic acid having from 1 to 5 carbon atoms).

4. The production method according to any one of claims 1 to 3, wherein X is chlorine atom in the 1,2-epoxy-3-halogenopropane represented by the general formula (I) and 1-halogeno-3-l-menthoxypropan-2-ol represented by the general formula (II).

5. The production method according to any one of claims 1 to 3, wherein configuration of the 2-position of the propane moiety is (R)-form in the 1,2-epoxy-3-halogenopropane represented by the general formula (I), and configuration of the 2-position of the propane moiety is (S)-form in the 1-halogeno-3-l-menthoxypropan-2-ol represented by the general formula (II), 1-acyloxy-2-substituted-3-l-menthoxypropane represented by the general formula (III) and 3-l-menthoxypropane-1,2-diol represented by the general formula (IV).

6. The production method according to any one of claims 1 to 3, wherein $R^1$ is acetyl group and $R^2$ is hydrogen atom or acetyl group in the general formula (III).

7. A 1-acyloxy-2-substituted-3-l-menthoxypropane represented by the following general formula (III):

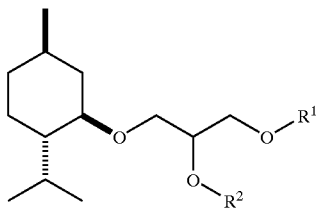
(III)

(wherein $R^1$ represents an acyl group derived from an aliphatic carboxylic acid having from 1 to 5 carbon atoms, and $R^2$ represents hydrogen atom or an acyl group derived from an aliphatic carboxylic acid having from 1 to 5 carbon atoms).

8. A 1-acetoxy-2-substituted-3-l-menthoxypropane represented by the following general formula (IIIa):

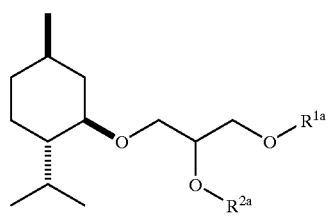
(IIIa)

(wherein $R^{1a}$ represents acetyl group, and $R^{2a}$ represents hydrogen atom or acetyl group).

9. A (2S)-1-acyloxy-2-substituted-3-l-menthoxypropane represented by the following general formula (III'):

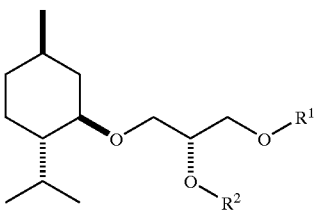
(III')

(wherein $R^1$ represents an acyl group derived from an aliphatic carboxylic acid having from 1 to 5 carbon atoms, and $R^2$ represents hydrogen atom or an acyl group derived from an aliphatic carboxylic acid having from 1 to 5 carbon atoms).

10. A (2S)-1-acetoxy-2-substituted-3-l-menthoxypropane represented by the following general formula (IIIa'):

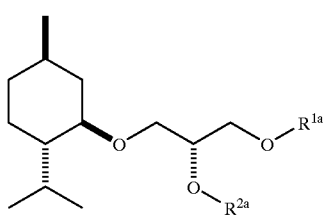
(IIIa')

(wherein $R^{1a}$ represents acetyl group, and $R^{2a}$ represents hydrogen atom or acetyl group).

* * * * *